United States Patent [19]
Purnell et al.

[11] Patent Number: 4,781,182
[45] Date of Patent: Nov. 1, 1988

[54] APPARATUS AND METHOD FOR USE IN PERFORMING A SURGICAL OPERATION

[76] Inventors: Mark L. Purnell, 323 Free Silver Dr.; Robert R. Odén, P. O. Box 660, both of Aspen, Colo. 81611; William L. McCune, 1739 W. 35th, Denver, Colo. 80211; Michael E. Berkeley, 1695 Silver King Dr.; Aspen, Colo. 81611

[21] Appl. No.: 915,122

[22] Filed: Oct. 3, 1986

[51] Int. Cl.⁴ .............................................. A61F 5/04
[52] U.S. Cl. .......................... 128/92 VD; 128/92 VZ
[58] Field of Search ......... 128/92 V, 92 VZ, 92 VW, 128/92 VD, 92 VL, 92 YF, 92 YJ, 92 YC, 92 YD, 305.1, 305, 346

[56] References Cited

U.S. PATENT DOCUMENTS

| 4,509,516 | 4/1985 | Richmond . |
| 4,524,766 | 6/1985 | Petersen . |
| 4,535,768 | 8/1985 | Hourahame et al. ............ 128/305.1 |
| 4,566,448 | 1/1986 | Rohr, Jr. . |
| 4,567,885 | 2/1986 | Androphy . |
| 4,567,886 | 2/1986 | Petersen . |

FOREIGN PATENT DOCUMENTS 2147504 5/1985 United Kingdom .......... 128/92 VD

OTHER PUBLICATIONS

William G. Clancy, Jr., M.D. Anterior Cruciate Ligament Reconstruction Technique.
Mark B. Coventry, M.D. Osteotomy about the Knee for Degenerative and Rheumatoid Arthritis Primary Examiner—C. Fred Rosenbaum
Assistant Examiner—M. Colosimo
Attorney, Agent, or Firm—Klaas & Law

[57] ABSTRACT

Apparatus and methods for use in performing surgical operations such as anterior or posterior cruciate ligament reconstructions wherein the apparatus has means for positioning a target area at the center of a an arc of a circle so that when the target area is positioned at a location relative to the anatomical center of the original attachment of the cruciate ligaments on the tibia and femur bones, kirschner wires may be pushed through guide means having a longitudinal axis coinciding with a ray emanating from the center of the circle and indicate the proper location for holes in the tibia and femur for the proper attachment of a cruciate ligament graft substitute. The apparatus is also used in the placement of kirschner wires to serve as guide wires in the performance of an osteotomy.

10 Claims, 3 Drawing Sheets

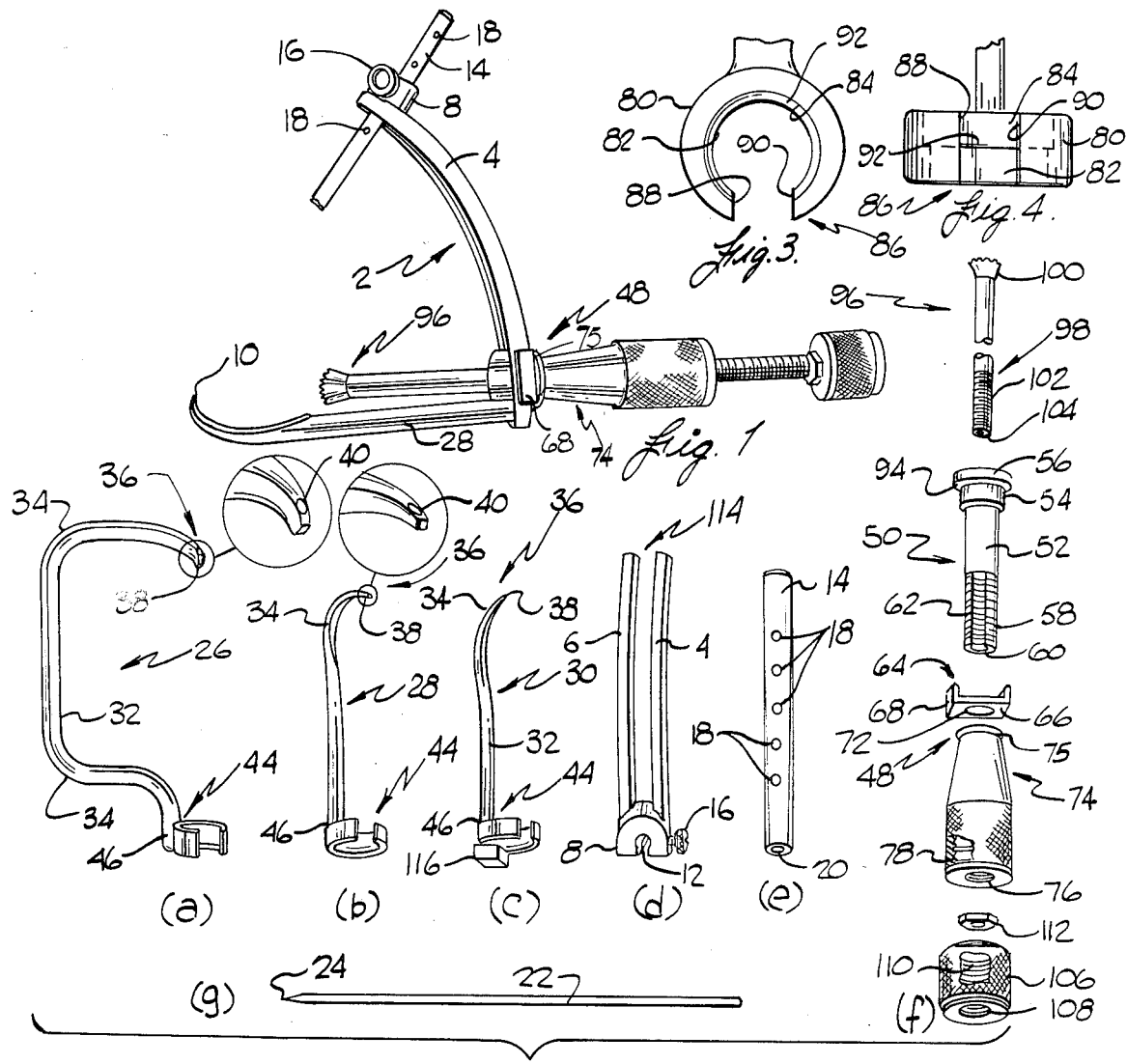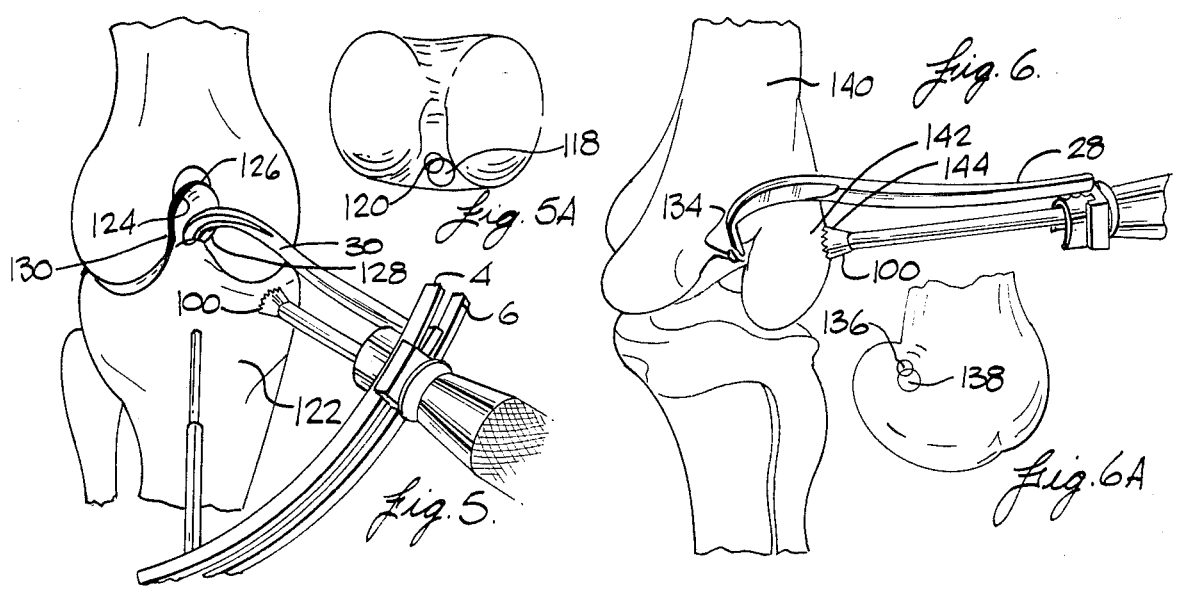

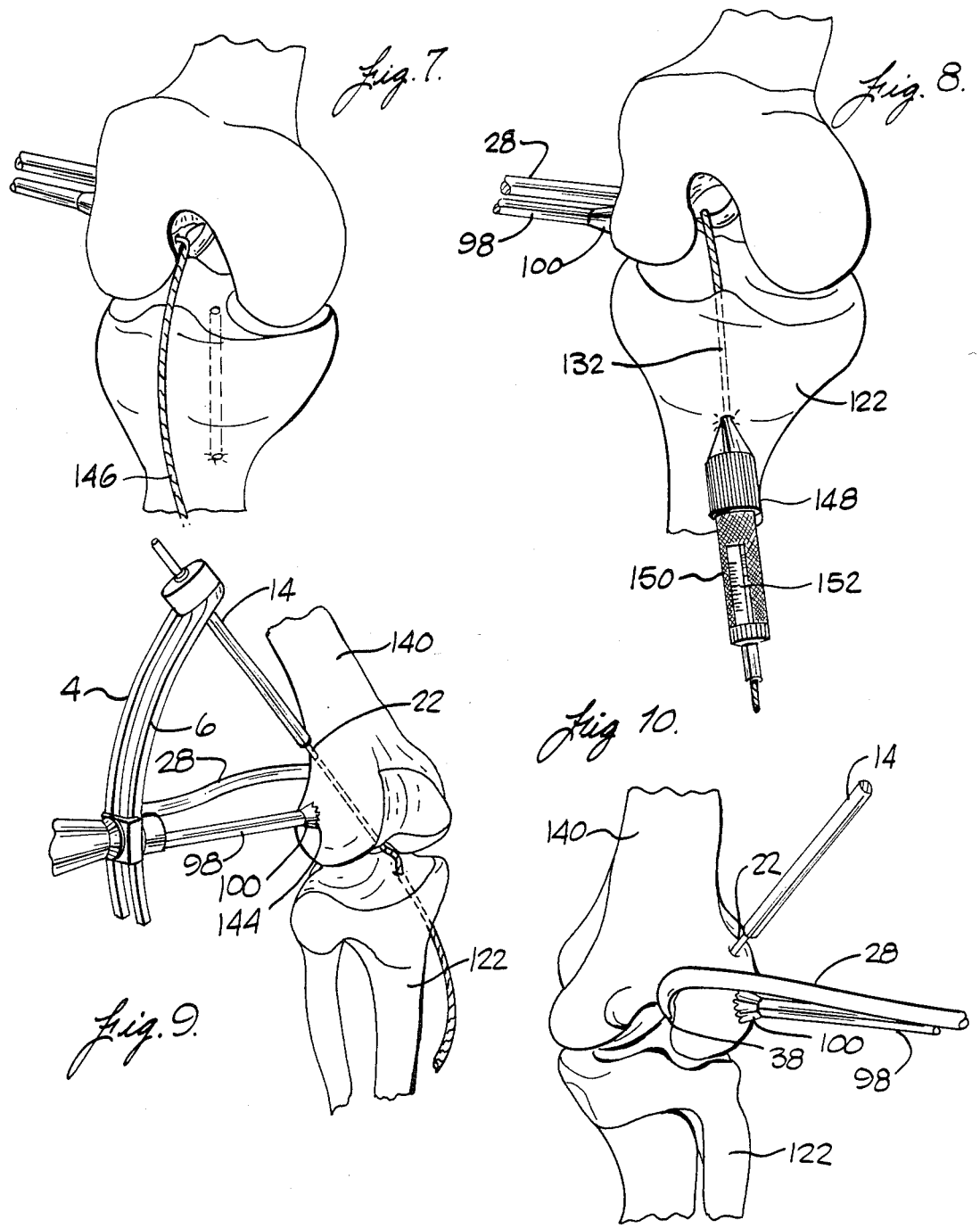

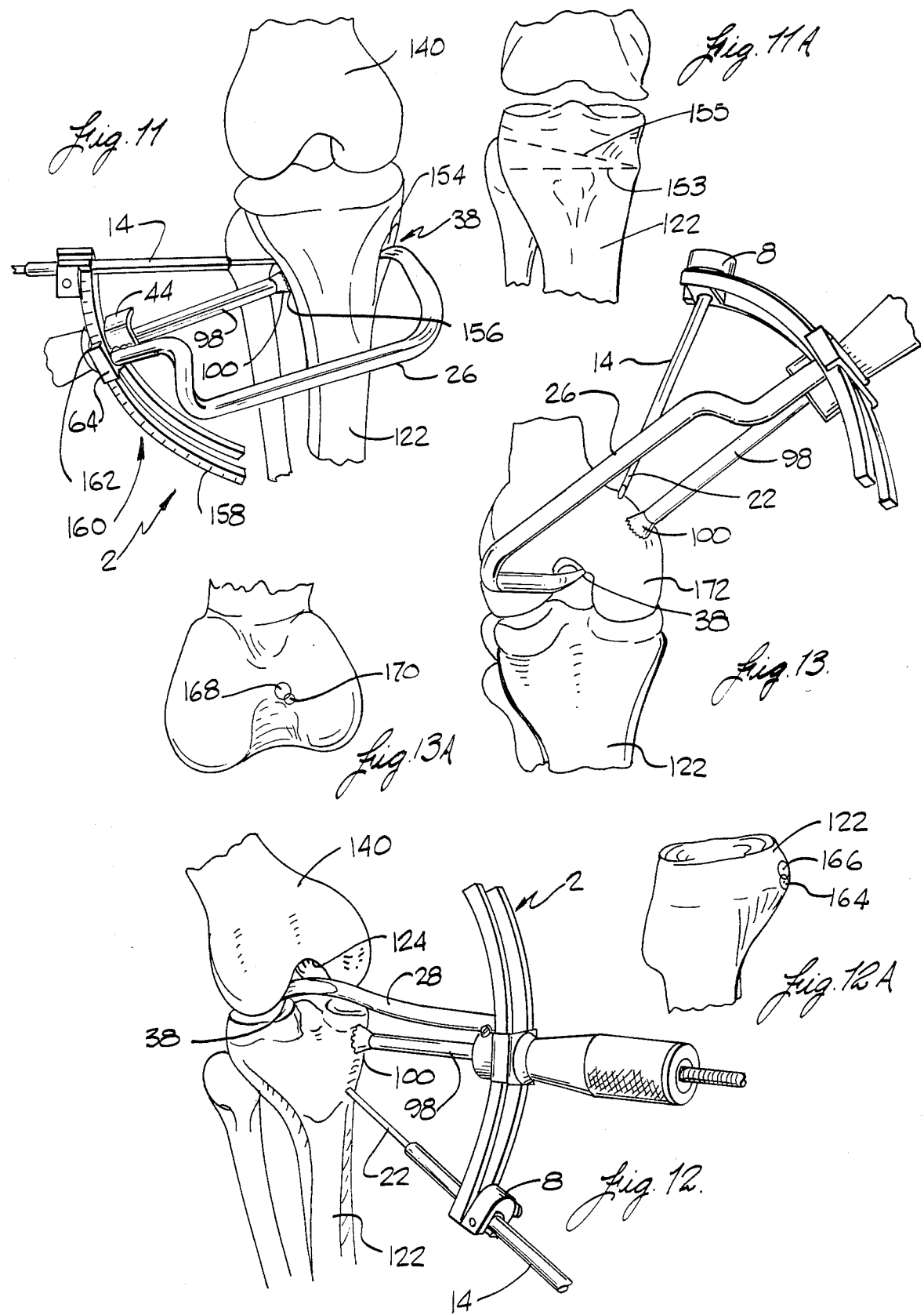

APPARATUS AND METHOD FOR USE IN PERFORMING A SURGICAL OPERATION

FIELD OF THE INVENTION

This invention is directed generally to surgical apparatus and methods of using such apparatus and more particularly to surgical apparatus and methods for the reconstruction of anterior or posterior cruciate ligaments in the human knee and the performance of osteotomies to an accurate angulation.

BACKGROUND OF THE INVENTION

The anterior cruciate ligament is the second largest ligament in the knee. The only ligament structure of greater strength and size is the posterior cruciate ligament. The anterior cruciate ligament and posterior cruciate ligament act in conjunction to provide both static and dynamic stability to the knee function. In the static mode, the anterior cruciate ligament prevents anterior subluxation of the tibia on the femur. In a similar fashion, the posterior cruciate ligament prevents posterior subluxation of the tibia on the femur. When both the anterior cruciate ligament and posterior cruciate ligament are intact, they work in conjunction with the medial collateral ligament, latera collateral ligament and bony and cartilagenous materials in the knee to prevent varus and valgus deformity.

In a dynamic mode, the cruciate ligaments are the foundation of knee joint kinematics. Together with the bony confines of the condyles they not only determine the type of motion that will occur, but also provide stability from outside forces, preventing subluxation during the range of motion. Human knee motion does not occur as a simple hinged model, but rather combines gliding, sliding and rotation. To accomplish this, the anterior and posterior cruciate ligament function according to the principles of a crossed four bar linkage. Considering the knee in a single plane, the movement of the anterior cruciate and posterior cruciate ligament origins and insertions define circular arcs during flexion and extension according to the principles of a crossed four bar linkage. This four bar linkage is closely related to and dependent upon the bony constraints of the surfaces of the tibia and femur. It is for this reason that the anatomic origin and insertion of both the anterior cruciate ligament and posterior cruciate ligament is so crucial. Any attempt at reconstructing the anterior and posterior cruciate ligament must consider these points of the four bar linkage system if successful reconstruction is to be obtained. Of the four points on the crossed four bar linkage system, the femoral origins are the most crucial. If anterior cruciate or posterior cruciate ligament reconstruction is performed in the appropriate location, then normal motion and stability can be reconstructed. If, however, these points are deviated from in reconstruction, either the ligament will be too loose to function in an anatomic fashion or too tight to allow normal motion. If the latter occurs, as normal range of motion is regained, the ligament substitute will ultimately fail. This invention facilitates the determination of the isometric cruciate ligament points of femoral origin for anterior and posterior cruciate ligament reconstruction.

Osteotomy of the upper part of the tibia is described beginning on page 30 in an article by Mark B. Coventry, M.D. published in "The Journal Of Bone And Joint Surgery" in Vol. 55-A, No. 1, Jan. 1973, which is incorporated herein by reference. As illustrated in FIG. 7-B on page 33 of Coventry, the osteotomy of the upper part of the tibia is done to remove a wedge of the tibia, which is then closed and retained in place by a stepped staple.

BRIEF SUMMARY OF THE INVENTION

This invention provides apparatus and method for the reconstruction of the anterior and posterior cruciate ligaments of the human knee and in the performance of osteotomies. The invention greatly facilitates the proper location of the isometric cruciate ligament points of femoral origin for the anterior and posterior cruciate ligaments and the exact angle for the osteotomy.

The apparatus of the preferred embodiment of the invention comprises an arcuate support means comprising a pair of arcuate tracks that are attached to a guide means which holds the tracks in a spaced apart parallel relationship. The arcuate tracks have a longitudinal axis which is an arc of a circle. A passageway' extends through the guide means and has a longitudinal axis coinciding with a ray from the center of the arc of the circle. A pin sleeve is mounted in the guide means and has a passageway extending therethrough with the longitudinal axis thereof coinciding with the longitudinal axis of the guide means. A plurality of targeting hooks are provided for use during different surgical procedures during the reconstruction of the anterior or posterior cruciate ligaments or in the performance of an osteotomy. Each targeting hook comprises an elongated body having curved portions, a target area at a first end portion and an attachment means at a second end portion for use in cooperation with securing means for securing the targeting hook at a desired location on the arcuate tracks so that its target area coincides with the center of the circle from which the arc is taken.

The securing means includes a hollow elongated rod having a cross-sectional configuration so that a central portion thereof ma be located between the arcuate tracks and is provided with a first and a second outwardly projecting flange portion of different sizes but similarly shaped cross-sectional configurations located adjacent to one end thereof with the second flange portion having the greater cross-sectional configuration located closer to the one end. The other end of the hollow elongated rod is provided with an internal and an external threaded portion. An open ended C-shaped angle member having a central opening is mounted on the central portion of the hollow elongated rod so that the open ended C-shaped angle member can have sliding movement over the hollow elongated rod. The legs of the C-shaped angle member are spaced apart a distance slightly greater than the distance between the outer lateral surfaces of the arcuate tracks so that the C-shaped angle member can be positioned over the tracks. The securing means also includes a force applying means having an inner passageway extending therethrough and having a portion thereof provided with threads for threaded engagement with the externally threaded portion of the hollow elongated rod. The force applying means has a force applying end adapted to contact the open ended C-shaped angle member so that rotation of the force applying means relative to the hollow elongated rod will move the open ended C-shaped angle member along the hollow elongated rod.

The attachment means on each of the targeting hooks comprises a hollow body member having an internal cross-sectional configuration similar in shape to but slightly larger than the first flange portion of the hollow elongated rod and similar to but smaller than the second flange portion so that when the attachment means is positioned on the hollow elongated rod, relative movement therebetween in one direction will be limited. A longitudinally extending slot is formed in the hollow body member with the width o the slot being greater than the portion of the hollow elongated rod but less than the first flange portion thereof. The attachment means is assembled on the hollow elongated body by inserting the portion of the hollow elongated body through the slot and then causing relative longitudinal movement between the hollow body portion and the hollow elongated rod until it contacts the second flange portion to prevent further movement. The edges defining the slot prevent passage of the first flange portion therethrough.

A clamping means is also provided and comprises a hollow elongated clamping rod having a freely rotatable foot portion adjacent to one end thereof and an externally threaded portion adjacent to the other end thereof and when in use, the externally threaded portion is in threaded engagement with the internally threaded portion of the hollow elongated rod. Knob means are provided on the other end of the hollow elongated clamping rod so that the hollow elongated clamping rod may be rotated relative to the hollow elongated rod and cause longitudinal movement of the hollow elongated clamping rod. The longitudinal axis of the hollow elongated rod coincides with a ray emanating from the center of the circle from which the arc is taken.

In performing a reconstruction of the anterior cruciate ligament the tibial drill hole is first prepared. A tibial targeting hook is secured to the hollow elongated rod using the attachment means. The knee is bent to the 90 degree position. Using conventional arthroscopic surgical procedures, the tibial targeting hook is inserted through an arthroscopic portal and the target area thereof is visually placed at a position anterior and medial to the anatomic center of the original anterior cruciate ligament on the tibia as described in an article published in 1983 by William G. Clancy, Jr., M.D., entitled "Anterior Cruciate Ligament Reconstruction Technique", which is incorporated herein by reference. The clamping means are actuated to clamp the tibial target hook in position. The arcuate tracks and the pin sleeve are moved until the pin sleeve is positioned at the proper angular relationship with the tibia. A kirschner wire is then passed through the passageway in the pin sleeve and is then operated in a conventional manner to move through the tibia until it strikes the target area of the targeting hook. The tibial targeting hook is removed and the position of the end of the kirschner wire that struck the target area is visually checked arthroscopically as the knee is brought into extension to ensure that the kirschner wire does not contact the anterior aspect of the intercondylar notch or the medial or lateral aspect of the intercondylar notch. If there is no contact, the kirschner wire is overdrilled with a reamer and the tibia bone hole is plugged. If contact occurs, the kirschner wire is repositioned using the same procedures. Using conventional surgical procedures, a non-absorbable suture is passed from the anterior aspect of the knee and intraarticular through the intercondylar notch and out of the posterior-lateral aspect of the knee. A femoral targeting hook is secured to the clamping means and one end of the suture is tied thereto at the target area thereof. Using conventional arthroscopical procedures, the femoral targeting hook is inserted through a posterior lateral incision and the target area thereof is visually placed in a position superior and lateral to the anatomic center of the original anterior cruciate ligament on the femur 140 as described in Clancy. The clamp is tightened into place around the lateral femoral condyle to hold the one end of the suture in place. The tibia hole is unplugged and the other end of the suture is passed therethrough and is affixed to an excursion measuring device which is mounted in a fixed location. The knee is then placed at 0, 30, 60 and 90 degrees and the movement of the portion of the suture between the target area of the femoral target hook and the attachment to the excursion device is observed. If the observed movement in any direction is 2 mm or less, the target area is in the correct location. If the observed movement is more than 2 mm, the clamp is loosened and the targeting hook is repositioned. The arcuate tracks and guide means are secured on the femoral target hook at the proper location so that holes in the tibia and femur will be generally parallel. A kirschner wire is then passed through the pin sleeve and moved in a conventional manner to move through the femoral bone until it strikes the target area of the targeting hook. The clamping means are loosened and the clamping means, the femoral target hook, the arcuate tracks and the guide means are removed to leave the kirschner wire in place. The kirschner wire is then overdrilled with a bone reamer. The anterior cruciate ligament graft substitute is then placed appropriately in the tibial and femoral holes and fixed in place as the surgeon desires.

The procedure in performing an osteotomy of the upper part of the tibia is to first determine the angle of the wedge that is to be removed. An osteotomy targeting hook is attached to the clamping means and the target area is placed at the level of the first cut and is then clamped in place so that the level of the first cut extends along the ray coinciding with the longitudinal axis of the hollow elongated clamping rod. The arcuate tracks and guide means are moved over the securing means until the scale on the arcuate tracks in cooperation with the edge of the C-shaped angle member indicates that the desired number of degrees for the second cut has been reached. The securing means are actuated to keep the pin sleeve at the proper location. The second cut extends along the ray coinciding with the longitudinal axis of the pin sleeve. Kirschner wires are then inserted through the pin sleeve and the hollow elongated clamping rod until they contact each other at the target area. The apparatus is removed leaving the kirschner wires in place to act as guides for a saw or osteotome.

The procedure in performing the reconstruction of a posterior cruciate ligament is similar to the above-described procedure for performing the reconstruction of the anterior cruciate ligament. The target are for the tibial passageway is inferior and lateral to the anatomic center of the original posterior cruciate ligament on the tibia and the target area for the femoral passageway is anterior and medial to the anatomic center of the original posterior cruciate ligament on the femur as described in Clancy.

It is an object of this invention to provide apparatus and method for the proper location of the tibial and femoral bone holes in the reconstruction of an anterior cruciate ligament or a posterior cruciate ligament.

It is another object of this invention to provide method and apparatus for the accurate placement of kirschner wires to serve as guides in the performance of an osteotomy.

Additional objects, advantages, and novel features of the invention are set forth in part in the description which follows which will be understood by those skilled in the art upon examination of the following or may be learned by practice of the invention. The objects and advantages of the invention may be realized and obtained by means of the instrumentalities and combinations particularly pointed out in the appended claims.

BRIEF DESCRIPTION OF THE DRAWING

FIG. 1 is a pictorial view of an assembled apparatus of a preferred embodiment of this invention;

FIG. 2(a) is a pictorial view of a targeting hook for tibial valgus osteotomy and posterior cruciate ligament reconstruction;

FIG. 2(b) is a pictorial view of a femoral targeting hook for anterior cruciate ligament reconstruction;

FIG. 2(c) is a pictorial view of a tibial targeting hook for anterior cruciate ligament reconstruction;

FIG. 2(d) is a pictorial view of the guide means and the arcuate support means of FIG. 1;

FIG. 2(e) is a pictorial view of the pin sleeve of FIG. 1;

FIG. 2(f) is an exploded view of the securing means and the clamping means with portions thereof in section;

FIGS. 2(g) is a pictorial view of a kirschner wire for use in this invention;

FIG. 3 is a top plan view of the attachment means of a targeting hook;

FIG. 4 is a front elevational view of FIG. 3;

FIG. 5 is a pictorial illustration of the knee bones from the anterior of the knee and illustrates the apparatus in place for drilling a tibial hole for anterior cruciate ligament reconstruction;

FIG. 5(a) illustrates the location for the target area on the tibia for anterior cruciate ligament reconstruction;

FIG. 6 is a pictorial illustration of the knee bones, from the posterior of the knee and illustrates the positioning of the femoral targeting hook with a suture tied to the tip for anterior cruciate ligament reconstruction;

FIG. 6(a) illustrates the location for the target area on the femur for an anterior cruciate ligament reconstruction;

FIG. 7 is a pictorial illustration of the knee bones with the knee flexed and the femoral targeting hook clamped to the lateral femoral condyle and the suture passed through the femoral tunnel and out the anterior aspect of the knee;

FIG. 8 is a pictorial illustration similar to FIG. 7 with the suture passed through the tibial hole and secured to an excursion device;

FIG. 9 is a pictorial illustration of the knee bones from the anterior of the knee and illustrates the apparatus in place for drilling the femoral hole for anterior cruciate ligament reconstruction;

FIG. 10 is a pictorial illustration similar to FIG. 9 from the posterior of the knee;

FIG. 11 is a pictorial illustration of the knee bones with the apparatus in place for use in an osteotomy;

FIG. 11(a) illustrates the wedge to be removed;

FIG. 12 is a pictorial illustration of the knee bones with the apparatus in place for drilling a tibial hole for posterior cruciate ligament reconstruction;

FIG. 12(a) illustrates the location of the target area on the tibia for posterior cruciate ligament reconstruction;

FIG. 13 is a pictorial illustration of the knee bones with the apparatus in place for drilling a femoral hole for posterior cruciate ligament reconstruction; and FIG. 13(a) illustrates the location of the target area on the femur for posterior cruciate ligament reconstruction.

DETAILED DESCRIPTION OF THE INVENTION

In FIGS. 1 and 2, there is illustrated a preferred embodiment of the invention and various targeting hooks for use therewith. The apparatus comprises an arcuate support means 2 comprising a pair of spaced apart arcuate tracks 4 and 6 secured in fixed parallel relationship to a guide means 8. The space between the arcuate tracks 4 and 6 has a longitudinal axis which is an arc of a circle having a center at 10. The arcuate tracks 4 and 6 are preferably square in cross-sectional configuration but may have other configurations. The guide means 8 has a passageway 12 extending therethrough which has a longitudinal axis coinciding with a ray emanating from the center 10. A pin sleeve 14 is positioned in the guide means 8 and is held in place by a set screw 16 in threaded engagement in the guide means 8. If desired, the outer surface of the pin sleeve 14 can be provided with detents 18 for receiving the tip of the set screw 16 for preventing relative movement between the pin sleeve 14 and the guide means 8. A passageway 20 extends through the pin sleeve 14 and has a longitudinal axis coinciding with the longitudinal axis of the guide means 8. As described below, the passageway 20 functions as a guide means for a kirschner wire such as the kirschner wire 22, illustrated in FIG. 2(g). The kirschner wire 22 has a pointed tip 24.

A plurality of targeting hooks, such as the targeting hooks 26, 28 and 30 illustrated in FIGS. 2(a), (b) and (c), may be used for different purposes in accordance with the invention. The targeting hook 26 is used for tibial valgus osteotomy and posterior cruciate ligament reconstruction. The targeting hook 28 is a femoral targeting hook used in anterior cruciate ligament reconstruction. The targeting hook 30 is a tibial targeting hook used in anterior cruciate ligament reconstruction. Each of the targeting hooks 26, 28 and 30 have an elongated body 32 having one or more curved portions 34 and a first end portion 36. A target area 38 is located in each first end portion 36 and may comprise a passageway 40 as in targeting hooks 26 and 28. Each target area 38 is located at the center 10 when a targeting hook is secured to the apparatus as illustrated in FIG. 1. Each of the targeting hooks 26, 28 and 30 is provided with an attachment means 44, described more fully below, on a second end portion 46 thereof.

The apparatus, as illustrated particularly in FIG. 2(f), includes securing means 48 including a hollow elongated rod 50 having a central portion 52 having a cross-sectional configuration permitting the central portion 52 to be located between the tracks 4 and 6. Adjacent to one end thereof, the hollow elongated rod 52 has first and second outwardly directed flange portions 54 and 56. Although the hollow elongated rod 50 and the first and second flange portions 54 may be of any shape, in the preferred embodiment of the invention they have generally cylindrical outer and inner surfaces. As illustrated in FIG. 2(f), the diameter of the first flange portion 54 is greater than the diameter of the central portion 52 and the diameter of the second flange portion 56 is greater than the diameter of the first flange portion 54. Adjacent to the other end thereof, the hollow elongated rod 50 has an externally threaded portion 58. The hollow elongated rod 50 has a central passageway 60 extending therethrough and preferably having a generally cylindrical inner surface having an internally threaded portion 62 adjacent to the other end of the hollow elongated rod 50. The securing means 48 further includes an open ended C-shaped angle member 64 having a central body portion 66 and spaced apart outwardly projecting legs 68 and 70. The distance between the inner surfaces of the legs 68 and 70 is slightly greater than the distance between the outer surfaces of the tracks 4 and 6 so that the C-shaped angle member 64 can be positioned over the tracks 4 and 6. The C-shaped angle member 64 is also provided with a central opening 72, preferably having a generally cylindrical inner surface having a diameter slightly greater than the diameter of the central portion 52 of the hollow elongated rod 50 so that the C-shaped angle member 66 can be slidably mounted on the central portion 52 but less than the diameter of the first flange portion 54 so as to limit the sliding movement. The securing means 48 further includes a force applying means 74 having a central passageway 76 extending therethrough, preferable having a generally cylindrical inner surface having a diameter slightly greater than the diameter of the central portion 52 of the hollow elongated rod 50, and having an internally threaded portion 78 for threaded engagement with the externally threaded portion 58 of the hollow elongated rod 50.

The attachment means 44 of each targeting hook, as illustrated in FIGS. 3 and 4, comprises a hollow body member 80 preferably having a pair of generally cylindrical inner surfaces 82 and 84 with the diameter of the inner surface 82 being greater than the diameter of the first flange portion 54 but less than the diameter of the second flange portion 56 and the diameter of the inner surface 84 being greater than the diameter of the second flange portion 56. The hollow body member 80 has a longitudinally extending slot 86 therethrough with the distance between the edges 88 and 90 of the slot 86 being greater than the diameter of the central portion 52 of the hollow elongated rod 50 but less than the diameter of the first flange portion 54. This structure permits the attachment means 44 to be moved transversely over the central portion 52 and then longitudinally over the first flange portion 54 until the surface 92 between the generally cylindrical inner surfaces 82 and 84 contacts the shoulder 94 between the first and second flange portions 54 and 56 to limit the longitudinal movement thereof. In this position, the edges 88 and 90 of the slot 86 prevent relative transverse movement between the hollow body member 80 and the hollow elongated rod 50.

The apparatus of FIG. 1 also includes clamping means 96, illustrated particularly in FIG. 2(f), comprising a hollow elongated clamping rod 98, preferably having a generally cylindrical outer surface, having an enlarged foot portion 100 adjacent to one end thereof and an externally threaded portion 102 for threaded engagement with the internally threaded portion 62 of the hollow elongated rod 54. The foot portion 100 is rotatably mounted on the elongated clamping rod 98 by conventional means such as a flange in a groove. The hollow elongated clamping rod 98 has a diameter slightly less than the diameter of the passageway 60 so that it may be moved longitudinally through the central passageway 60. The externally threaded portion 102 is in engagement with the internally threaded portion 62 of the hollow elongated rod 50 for a purpose described below. A central passageway 104, preferably having a generally cylindrical inner surface, extends through the hollow elongated clamping rod 98 so that a kirschner wire 22 may be passed therethrough. The longitudinal axis of the central passageway 104 coincides with a ray emanating from the center 10 and intersects the target area 38 of any targeting hook attached thereto. Knob means 106 are provided for rotating the hollow elongated clamping rod 98 and have a central passageway 108 extending therethrough and having internal threads 110 for threaded engagement with the externally threaded portion 102. A lock nut 112 is provided for securing the knob means 106 to the hollow elongated rod 98. As illustrated in FIGS. 1 and 2, the force applying means 76 and the knob means 106 are provided with knurled surfaces to facilitate rotation thereof.

The apparatus illustrated in FIG. 1 may be assembled by first securing a pin sleeve 14 in the guide means 8. The C-shaped angle member 64 is then placed over the hollow elongated rod 50 which is then inserted into the central passageway 76 of the force applying means 74 which is rotated relative to the hollow elongated rod 50 in an amount to form a partially threaded relationship between the internally threaded portion 78 and the externally threaded portion 58. The hollow elongated clamping rod 98 is then inserted into the passageway 60 and rotated so that the externally threaded portion 102 will move into engagement with the internally threaded portion 62 of the hollow elongated rod 50 and, as illustrated in FIGS. 1 and 2, and after continued rotation will eventually project outwardly from the force applying means 74 having a force applying end 75. The knob means 106 is then secured to the hollow elongated clamping rod 98 using the lock nut 112. The externally threaded portion 102 is of sufficient length to ensure engagement with the internally threaded portion 62 for all possible locations of the foot portion 100. If desired, the entire outer cylindrical surface of the hollow elongated clamping rod 98 may be threaded. A targeting hook, such as the targeting hook 28, is then positioned on the hollow elongated rod by transversely moving the central portion 52 through the slot 86 and then causing relative longitudinal movement until the surface 92 contacts the shoulder 94. The central portion 52 is then inserted through the open ended portion 114 between the tracks 4 and 6 and moved to a desired location. The force applying means 74 is then rotated to move the C-shaped angle member 64 to a position over the tracks 4 and 6 and rotation is continued until the tracks 4 and 6 are firmly clamped between the attachment means 44 of the targeting hook and the C-shaped angle member 64. The attachment means 44 of targeting hooks 26 and 28 will permit relative rotation between the hollow body portion 82 and the first flange portion 54 until the firmly clamped position is reached. However, the attachment means 44 of the targeting hook 30 is provided with a projection 116 that is located between the tracks 4 and cooperates therewith for preventing relative rotation between the hollow body member 80 and the first flange portion 54. When it is desired to secure the apparatus to an object, the object is positioned between the foot portion 100 and the target area 38 and the knob means 106 is rotated to move the foot portion 100 toward the target area 38 until the object is clamped therebetween. In this assembled relationship, a ray from the target area 38 will coincide with the longitudinal axis of the pin sleeve 14 and another ray from the target area 38 will coincide with the longitudinal axis of the hollow elongated clamping rod 98.

In some instances, such as that illustrated in FIG. 6, the securing means 48, a targeting hook, such as 28, and the clamping means 96 are used together. The force applying means 74 are loosened and the arcuate tracks are removed. The force applying means 74 are actuated to move the C-shaped angle member 64 into contact with the attachment means 44. Continued rotation of the force applying means 74 moves the surface 92 and the shoulder 94 into an abutting relationship. Rotation of the force applying means 74 is continued until the hollow body member 80 is firmly secured between the second flange portion 56 and the C-shaped angle member 64. In this assembly, a ray from the target area 38 coincides with the longitudinal axis of the hollow elongated clamping rod 98.

The use of the apparatus to perform a surgical procedure involving the reconstruction of an anterior cruciate ligament is illustrated generally in FIGS. 5–10. In these illustrations only the general outline of the knee bones have been used. The various parts of the body associated with the knee joint have not been illustrated. A tibial targeting hook 30 is secured to the tracks 4 and 6 with the foot portion 100 of the elongated clamping rod 98 in a retracted position close to the securing means 48. Using conventional arthroscopic surgical procedures and with the knee at a 90 degree position, the first end portion of the tibial targeting hook 30 is passed through an arthroscopic portal and the target area 38 thereof is visually placed at a position 118 anterior and medial to the anatomic center 120 of the original anterior cruciate ligament, as described in Clancy. The clamping means 96 are actuated to move the foot portion 100 to a clamping position, illustrated in FIG. 5 as being against the tibia 122. A kirschner wire 22 having a diameter of about 2 mm, is inserted through the passageway 20 in the pin sleeve 14 and in a conventional manner moved through the tibia 122 and into a position against the target are 38 in the intercondylar notch 124. The tibial target hook 30 and its associated apparatus, as in FIG. 1, is removed leaving the kirschner wire 22 in place in the knee. The knee is extended to a straight position, zero degrees of flex, and the location of the kirschner wire is visually checked arthroscopically as the knee is moved to the extended position to ensure that the kirschner wire does not contact the anterior aspect 126 of the intercondylar notch 124 or the medial 128 or lateral 130 aspect of the intercondylar notch 120. If no contact is made, the kirschner wire 22 is overdrilled with a reamer, having a diameter of about 9 mm, and the tibia bone hole is plugged. If contact occurs, the kirschner wire is repositioned using the same procedures Using conventional arthroscopic procedures, a nonabsorbable suture 132 (FIG. 7) is passed from the anterior aspect of the knee, through the intercondylar notch 124 and out of the posterior-lateral aspect of the knee. A femoral targeting hook 28 is secured between the C-shaped angle member 64 and the second flange portion 56 and the elongated clamping rod 98 is moved to a retracted position. One end 134 of the suture 132 is tied to the target area 40 of the femoral targeting hook 32 which, using conventional arthroscopic procedures, is then inserted through a posterior lateral incision and the target area 38 thereof is visually placed in a position 136 superior and lateral to the anatomic center 138 of the original anterior cruciate ligament on the femur 140, as described in Clancy. The elongated clamping rod 98 is rotated so that the lateral femoral condyle 142 is clamped between the foot portion 100 and the target area 38 to hold the one end 134 of the suture 132 in place. As illustrated in FIG. 6, the foot portion 100 is provided with serrations 144 so as to prevent relative movement between the foot portion 100 and the bone as the clamping rod 98 is continued to be rotated so that the proper clamping force may be applied. Using conventional arthroscopic procedures, the tibia hole is unplugged and the other end 146 of the suture is passed therethrough and the suture 132 is affixed to an excursion device 148, FIG. 8. Sufficient tension is applied to the suture 132 so that the excursion device 148 is held in a fixed position against the tibia 122. The excursion device 148 has a scale 150 and a movable pointer 152 to indicate any movement of the suture 132. An isometric test is performed by placing the knee at 0, 30, 60 and 90 degrees and the movement of the portion of the suture between the target area of the femoral targeting hook and the attachment to the excursion device is observed. If the observed movement is 2 mm or less, the target area is at the isometric point. If the observed movement is more than 2 mm, the clamp is loosened and the targeting hook 28 is repositioned. If the position of the target area 38 is correct, the force applying means 74 are rotated so that the C-shaped angle member 64 may be moved and the central portion 52 may be inserted through the open ended portion 114 of the arcuate tracks so that the guide means 8 may be secured on the femoral target hook at the proper location so that holes in the tibia and femur are generally parallel. A kirschner wire, having a diameter of about 2 mm, is then passed through the pin sleeve 14 and moved in a conventional manner to move through the femoral bone. The clamping means are loosened and the clamping means, the femoral target hook, the arcuate tracks and the guide means are removed to leave the kirschner wire in place. The kirschner wire is then overdrilled with a bone reamer, having a diameter of about 9 mm. The anterior cruciate ligament graft substitute is then placed appropriately in the tibial and femoral holes and fixed in place as the surgeon desires.

In FIG. 11, the apparatus is illustrated in position for performing an osteotomy operation so that kirschner wires can be placed through both the pin sleeve 14 and the clamping rod 98 and through the tibia 122 so as to serve as guides for a saw or an osteotome. Using standard procedures, such as those described in Coventry, the angle of the wedge that is to be removed is determined. This indicates the path through the tibia for the first cut 153 and the second cut 155 as illustrated in FIG. 11(a). An osteotomy target hook 26 is attached to the hollow elongated rod 50 using the attachment means and the C-shaped angle member 64. The target area 38 is placed at the level of the desired first osteotomy cut 153 on the closed or convex side 154 of the osteotomy. The clamping rod 98 is rotated to move the foot portion 100 into place on the open or concave side 156 of the osteotomy. Rotation of the clamping rod 98 is continued until target area 38 is firmly clamped in position. The force applying means 74 is loosened and the C-shaped angle member is moved over the elongated hollow rod 50 so that the open ended portion 114 of the arcuate support means 2 can be moved over the central portion 52. The side 158 of the arcuate support means 2 is provided with angular degree markings 160 for cooperation with the edge 162 of the C-shaped angle member 64. When the desired number of degrees is reached for the angle of the second cut 155 as determined by the ray passing through the pin sleeve 14, the force applying means 74 are actuated to clamp the arcuate support means 2 in place. Kirschner wires 22 are inserted through the pin sleeve 14 and the clamping rod 98 until the points thereof strike the target area 38 or until the point of the second inserted kirschner wire 22 strikes the first inserted kirschner wire 22. The arcuate support means 2, the pin sleeve 14, the clamping means 98 and the targeting hook 26 are removed and X-rays are taken to ensure that the proper angular relationship for the kirschner wires has been obtained. Once this has been determined, the kirschner wires act as guides for a saw or an osteotome to perform the remaining aspect of the osteotomy. When utilized in an osteotomy, the apparatus of this invention assures that kirschner wires can be placed in the bone at a predetermined angle such that they intersect at a given point on the opposite side of the bone. In this fashion accurate osteotomies may be performed utilizing the kirschner wires as guides and ensuring the surgeon that the exact angle of the osteotomy is obtained and that the osteotomy removes no bone from the convex side of the osteotomy site.

The location of the apparatus for a reconstruction of the posterior cruciate ligament is illustrated in FIGS. 12 and 13. The procedures for performing a posterior cruciate ligament reconstruction are generally similar to those described above in relation to the performance of an anterior cruciate ligament reconstruction. Using a posterior medial arthroscopic portal, the location for the target area is identified on the posterior of the tibia 122. A targeting hook 28 is attached to the arcuate support means 2 and a pin sleeve 14 is secured in the guide means 8. The targeting hook 28 has been introduced through an anterior portal into the intercondylar notch 124 and the target area is positioned at a location 164, FIG. 12(a), inferior and lateral to the anatomic center 166 of the original posterior cruciate ligament. The clamping rod 98 is rotated so that a portion of the tibia 122 is clamped between the target area 38 and the foot portion 100 which is located at the anterior medial aspect of the tibia. A kirschner wire 22 is inserted through the pin sleeve 14 and through the tibia 122 until it strikes the target area 38. As described above, the apparatus is removed and the knee is arthroscopically viewed as it is extended to ensure that the kirschner wire has been properly located. The kirschner wire is then over-reamed.

As illustrated in FIG. 13, a different targeting hook 26, which is also used in performing an osteotomy, has been secured to the arcuate support means 2. As described above, one end of a suture has been secured to the target area 38 of the targeting hook 26 which is then introduced anteriorly and positioned at a location 168, FIG. 13(a), slightly anterior and lateral to the anatomic center 170 of the original posterior cruciate ligament. The clamping rod 98 is rotated so that a portion of the femoral condyle 172 is clamped between the foot portion 100 and the target area 38. As in the anterior cruciate ligament reconstruction procedure, one end of the suture is secured to the target area and the other end of the suture is then passed through the tibial hole and secured to an excursion device 148 in the same manner as described above. The knee is placed at 0, 30, 60 and 90 degrees and any movement of the suture as indicated on the scale 150 is observed. If any observed movement is 2 mm or less, the target area 38 has been properly located. A kirschner wire is then passed through the pin sleeve 14 and through a portion of the femur until it strikes the target area 38. The clamping means are loosened and the arcuate support means, the targeting hook, the guide and pin sleeve, the securing means and the clamping means are removed. The kirschner wire is then overdrilled with a bone reamer. The posterior cruciate ligament graft substitute is then placed appropriately in the tibial and femoral holes and fixed in place as the surgeon desires.

It is contemplated that the inventive concepts herein described may be variously otherwise embodied and it is intended that the appended claims be construed to include the alternative embodiments of the invention except insofar as limited by the prior art.

What is claimed is:

1. Apparatus for use in performing surgery on a portion of a body comprising:
   an arcuate support means having a longitudinal axis comprising an arc of a circle having a center;
   said arcuate support means having a first end portion and a second end portion;
   guide means secured to said first end portion;
   a passageway extending through said guide means and having a longitudinal axis coinciding with a ray from said center of said circle;
   pin sleeve means mounted and secured in said guide means;
   said pin sleeve means having a passageway extending therethrough and having a longitudinal axis coinciding with said longitudinal axis of said guide means so that drill means may be guided through said passageway and enter into said portion of said body;
   targeting means having a non-linear configuration and having a target area portion at one end thereof so that said target area portion may be positioned at a desired location inside said portion of said body and attachment means at the other end of said targeting means;
   releasable securing means for cooperating with said attachment means to secure said targeting means to said arcuate support means so that said target area portion is located at said center of said circle;
   clamping means movably mounted on said securing means for movement into contact with the outside of said portion of the body and to apply pressure thereto so as to cooperate with said securing means to hold said target area portion at said desired location; and
   said releasable securing means permitting movement of said arcuate support means and said guide means relative to said targeting means and said clamping means so that said pin sleeve means may be located so that said drill means will pass through said portion of said body at the proper angular relationship thereto and contact said target area portion.

2. Apparatus as in claim 1 wherein said arcuate support means comprises:
   a pair of spaced apart, parallel tracks;
   said guide means closing said first end portion between said tracks;

said guide means secured to said tracks and holding said tracks in said spaced apart parallel relationship;

said arc of said circle being located in the space between said spaced apart, parallel tracks; and an opening at said second end portion of said tracks for permitting objects to be positioned between said tracks.

3. Apparatus as in claim 2 wherein said targeting means comprises:

an elongated member having a first and a second end portion;

said target area being located at said first end portion of said elongated member; and attachment means at said second end portion of said elongated member.

4. Apparatus as in claim 3 wherein said securing means comprises:

a hollow elongated rod having a first end and a second end;

a central portion on said hollow elongated rod and having a cross-sectional configuration so that a portion thereof may be located between said tracks;

said hollow elongated rod having a first and a second flange portion projecting outwardly therefrom and having different sized but similar shaped cross-sectional configurations and located adjacent to one end of said hollow elongated rod with said second flange portion having a cross-sectional configuration greater than the cross-sectional configuration of said first flange portion and located between said first flange portion and said first end;

an abutment shoulder formed at the juncture of said first and second flange portions;

an externally threaded portion adjacent said second end of said end of said hollow elongated rod;

an open ended C-shaped angle member having a central opening having a cross-sectional configuration greater than the cross-sectional configuration of said central portion so that said open ended C-shaped angle member can be placed over said hollow elongated rod and have relative sliding movement thereof;

said open end ed C-shaped angle member being dimensioned so that said spaced apart, parallel tracks may be received therein;

force applying means having an inner passageway having an internally threaded portion for engagement with said externally threaded portion of said hollow elongated rod; and a force applying end on said force applying means adapted to contact said open ended C-shaped angle member so that when said force applying means is rotated relative to said hollow elongated rod, said open ended C-shaped angle member will be moved along said hollow elongated rod arcuate support means between said attachment means and said C-shaped angle member.

5. Apparatus as in claim 4 wherein said attachment means comprises:

a hollow body member having a portion of its internal cross-sectional configuration similar in shape to but slightly larger than said cross-sectional configuration of said second flange portion of said hollow elongated rod;

a longitudinal extending slot in said hollow body member, said slot being dimensioned so that said central portion of said hollow elongated rod may be moved through said slot and into and positioned within said hollow body member; and an inwardly projecting flange in said hollow body member and forming an abutment surface adapted to contact said abutment shoulder on said hollow elongated rod so as to prevent relative movement in one direction between said hollow body member and said hollow elongated rod.

6. Apparatus as in claim 5 and further comprising:

means for preventing relative rotational movement between said hollow body member and said hollow elongated rod.

7. Apparatus as in claim 5 wherein said clamping means comprises:

an internally threaded portion adjacent said second end of said hollow elongated rod;

a hollow elongated clamping rod having a foot portion adjacent one end thereof and an externally threaded portion adjacent the other end thereof;

said externally threaded portion of said hollow elongated clamping rod being in threaded engagement with said internally threaded portion of said hollow elongated rod so that rotation of said elongated clamping rod will cause axial movement thereof relative to said hollow elongated rod to move said foot portion toward or away from said target area so that said target area may be secured at a desired location on said portion of said body; and knob means secured to said other end of said elongated clamping rod for use in applying a rotational force to said elongated clamping rod.

8. Apparatus as in claim 7 wherein said target area comprises:

a tip on said first end portion.

9. Apparatus as in claim 7 wherein said target area comprises:

an opening extending through said first end portion.

10. Apparatus as in claim 7 and further comprising:

an inner passageway extending through said elongated clamping rod in an axial direction;

an opening passing through said knob means in alignment with said inner passageway; and said inner passageway having a longitudinal axis coinciding with a ray from said center of said circle.

* * * * *